(12) United States Patent
Koshinaka et al.

(10) Patent No.: US 12,189,745 B2
(45) Date of Patent: *Jan. 7, 2025

(54) ACOUSTIC PERSONAL AUTHENTICATION DEVICE, PERSONAL AUTHENTICATION METHOD, AND RECORDING MEDIUM

(71) Applicant: NEC CORPORATION, Tokyo (JP)

(72) Inventors: Takafumi Koshinaka, Tokyo (JP); Masahiro Saikou, Tokyo (JP); Takayuki Arakawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/345,711

(22) Filed: Jun. 30, 2023

(65) Prior Publication Data

US 2023/0409688 A1  Dec. 21, 2023

Related U.S. Application Data

(63) Continuation of application No. 16/333,829, filed on Mar. 15, 2019, now Pat. No. 11,734,399, which is a
(Continued)

(30) Foreign Application Priority Data

Sep. 16, 2016 (JP) ................................ 2016-181898

(51) Int. Cl.
*G06F 21/00* (2013.01)
*A61B 5/00* (2006.01)
(Continued)

(52) U.S. Cl.
CPC .............. *G06F 21/32* (2013.01); *A61B 5/117* (2013.01); *A61B 5/7405* (2013.01); *G07C 9/25* (2020.01);
(Continued)

(58) Field of Classification Search
CPC ....... G06F 21/32; A61B 5/117; A61B 5/7405; G07C 9/25; G07C 2009/00809;
(Continued)

(56) References Cited

U.S. PATENT DOCUMENTS 8,963,806 B1  2/2015  Starner et al.
9,147,053 B2  9/2015  Yamashita
(Continued)

FOREIGN PATENT DOCUMENTS

CN    105225304 A    1/2016
JP    2004-013831 A  1/2004
(Continued)

OTHER PUBLICATIONS

Communication dated Aug. 9, 2019 from European Patent Office in counterpart EP Application No. 17850852.9.
(Continued)

*Primary Examiner* — William A Corum, Jr.

(57) ABSTRACT

Provided is a personal authentication device capable of simply securing security with little psychological and physical burden of a user to be authenticated. Personal authentication device includes: storage that stores first and second identification information for identifying a user; analysis unit that analyzes information inputted to a user and generates the first identification information; transmission unit that transmits a first acoustic signal to a part of a user's head; observation unit that observes a second acoustic signal; calculation unit that calculates acoustic characteristics from the first and the second acoustic signal; extraction unit that extracts an acoustic feature amount from the acoustic characteristics as second identification information; and determination unit that determines the user to be identical when first identification information registered and the first identification information generated coincide with each other
(Continued)

and second identification information registered and the second identification information extracted coincide with each other.

9 Claims, 10 Drawing Sheets

Related U.S. Application Data continuation of application No. PCT/JP2017/032685, filed on Sep. 11, 2017.

(51) Int. Cl.
- *A61B 5/117* (2016.01)
- *G06F 21/32* (2013.01)
- *G07C 9/25* (2020.01)
- *G10L 17/00* (2013.01)
- *H04L 9/40* (2022.01)
- *G07C 9/00* (2020.01)
- *H04W 12/065* (2021.01)
- *H04W 12/65* (2021.01)

(52) U.S. Cl.
CPC .......... *G10L 17/00* (2013.01); *H04L 63/0861* (2013.01); *G07C 2009/00809* (2013.01); *H04L 2463/082* (2013.01); *H04W 12/065* (2021.01); *H04W 12/65* (2021.01)

(58) Field of Classification Search
CPC ................ G10L 17/00; H04L 63/0861; H04L 2463/082; H04W 12/065; H04W 12/65
See application file for complete search history.

(56) References Cited

U.S. PATENT DOCUMENTS

| | | | |
|---|---|---|---|
| 9,277,334 B1 | 3/2016 | Wong et al. | |
| 2007/0248242 A1 | 10/2007 | Ritter et al. | |
| 2009/0087003 A1 | 4/2009 | Zurek et al. | |
| 2010/0328033 A1 | 12/2010 | Kamei | |
| 2013/0236066 A1 | 9/2013 | Shubinsky et al. | |
| 2014/0282945 A1 | 9/2014 | Smith et al. | |
| 2015/0111537 A1* | 4/2015 | Vural | A61B 5/6898 455/411 |
| 2015/0168996 A1* | 6/2015 | Sharpe | H04L 63/0861 455/66.1 |
| 2015/0347734 A1 | 12/2015 | Beigi | |
| 2017/0078780 A1 | 3/2017 | Qian et al. | |
| 2017/0347180 A1* | 11/2017 | Petrank | G06F 3/165 |
| 2019/0213313 A1 | 7/2019 | Koshinaka et al. | |

FOREIGN PATENT DOCUMENTS

| | | | |
|---|---|---|---|
| JP | 2004-065363 A | 3/2004 | |
| JP | 2007-202869 A | 8/2007 | |
| JP | 2009-509575 A | 3/2009 | |
| JP | 2011-191832 A | 9/2011 | |
| JP | 2012-161628 A | 8/2012 | |
| WO | 2007034371 A2 | 3/2007 | |
| WO | 2009/104437 A1 | 8/2009 | |

OTHER PUBLICATIONS

Communication dated May 13, 2020, from the European Patent Office in application No. 17850852.9.
International Search Report of PCT/JP2017/032685 dated Nov. 21, 2017.
Written Opinion of the International Searching Authority of PCT/JP2017/032685 dated Nov. 21, 2017.
Extended European Search Report for EP Application No. 22159179.5, dated on Jun. 15, 2022.
Japanese Office Action for JP Application No. 2018-539708 mailed on Oct. 12, 2021 with English Translation.

* cited by examiner

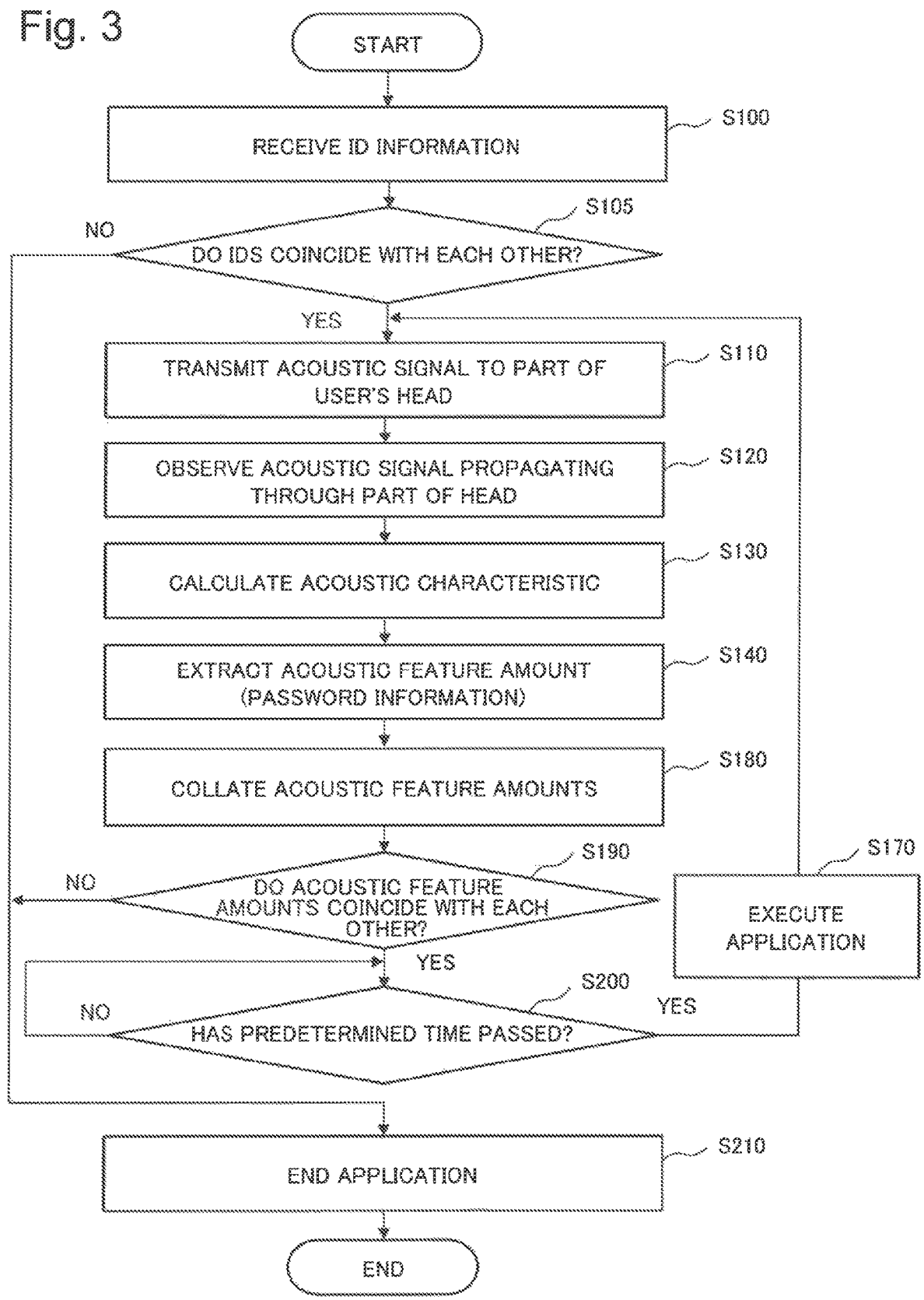

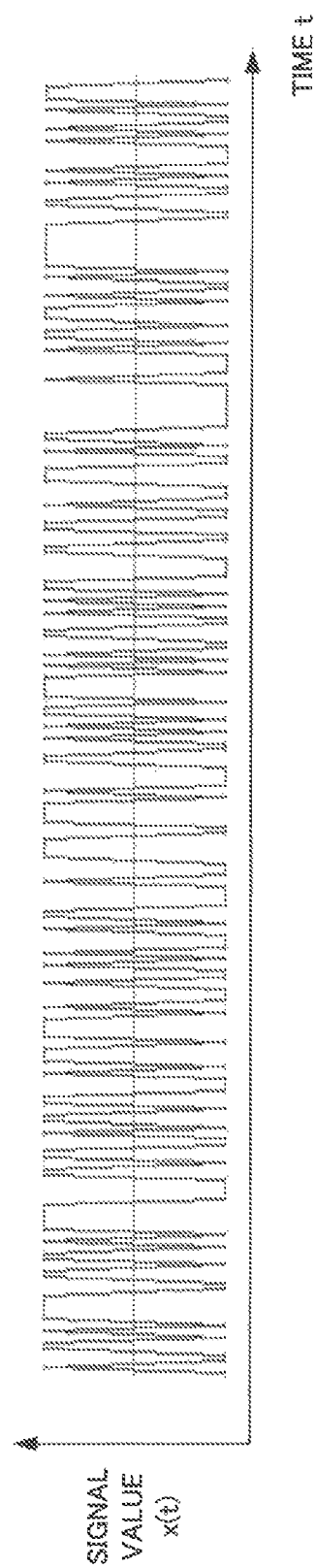

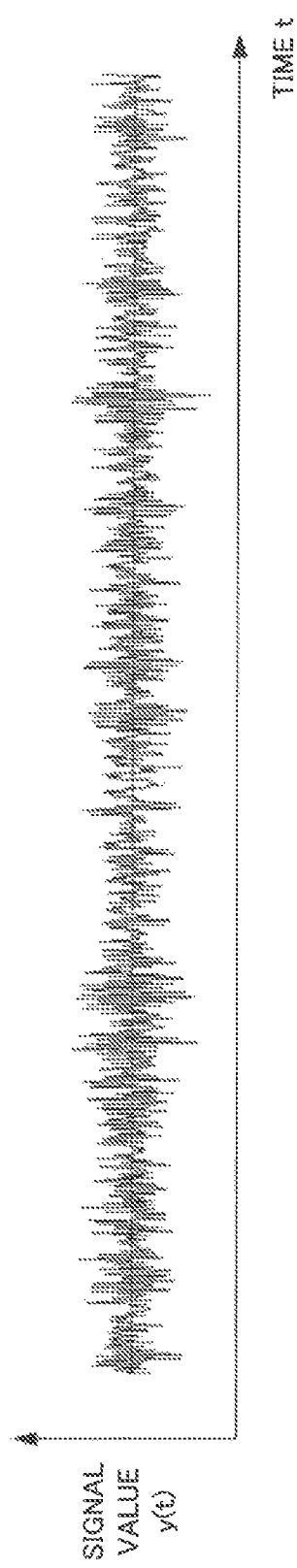

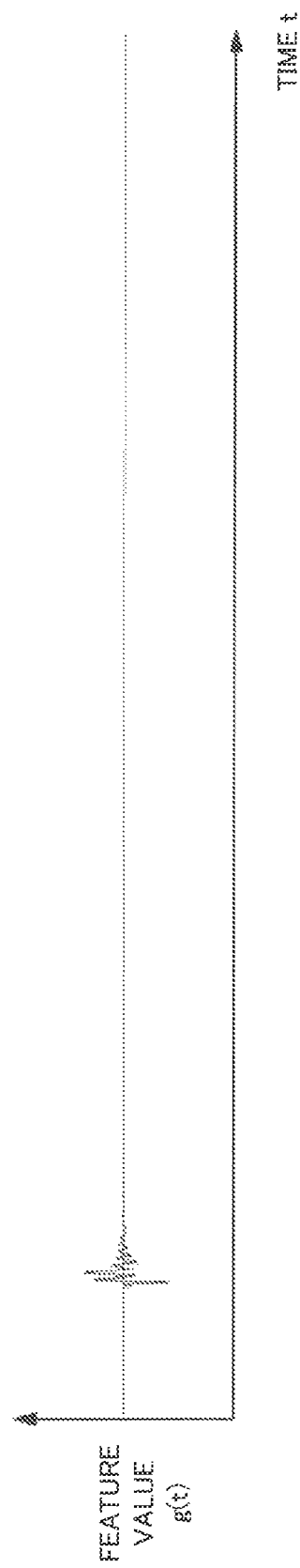

ACOUSTIC PERSONAL AUTHENTICATION DEVICE, PERSONAL AUTHENTICATION METHOD, AND RECORDING MEDIUM

CROSS REFERENCE TO RELATED APPLICATIONS

This application is a continuation of U.S. application Ser. No. 16/333,829, filed Mar. 15, 2019, which is a National Stage of International Application No. PCT/JP2017/032685 filed Sep. 11, 2017, claiming priority based on Japanese Patent Application No. 2016-181898 filed Sep. 16, 2016, the entire contents of which are incorporated herein by reference.

TECHNICAL FIELD

The present invention relates to a personal authentication device for authenticating an individual.

BACKGROUND ART

Since personal authentication (biometrics-based authentication) based on individual differences of a living body is less likely to leak or theft than passwords, it is increasingly introduced for the purpose of identifying individuals and confirming rights and for the purpose of security protection. As personal authentication technologies based on individual differences of a living body, there have been known technologies using e.g. a fingerprint, a vein, a face, an iris, and voice. Among them, a method using sound information can perform personal authentication with a general-purpose inexpensive device such as a telephone and a microphone without preparing a special device.

PTL 1 discloses a method in which a user is always monitored during log-in by using a biometrics authentication method based on a combination of a fingerprint, a face, a mouse movement.

PTL 2 discloses a signal transmitter that has interchangeability with an equipment to be used and can easily realize an inter-equipment authentication, and a personal authentication device that can constantly perform personal authentication (biometric authentication).

PTL 3 discloses a method for registering, authenticating, and identifying a human on the basis of acoustic characteristics of an ear canal.

CITATION LIST

Patent Literature

[PTL 1] Japanese Unexamined Patent Application Publication No. 2004-13831 A
[PTL 2] Japanese Unexamined Patent Application Publication No. 2004-65363 A
[PTL 3] Japanese Patent Application Laid-Open No. 2009-509575

SUMMARY OF INVENTION

Technical Problem

However, the biometric authentication disclosed in PTL 1 to 3 and performed at a predetermined place or time, has the following problems.

Firstly, in the case of personal authentication performed by acquiring biological information at a predetermined place or time, there is a problem that a user is forced to do an operation for performing authentication. For example, in the case of personal authentication using a fingerprint or a vein, an operation of a user such as putting his/her finger on a dedicated scanner is necessary. Furthermore, in the case of personal authentication using a face or an iris, an operation of a user such as turning a face to a camera is necessary. Furthermore, in the case of personal authentication using voice or bone conduction sound, an operation of a user such as speaking a password is necessary. Therefore, a user has a psychological and physical burden in each authentication. Moreover, in the case of personal authentication performed by acquiring biological information at a predetermined place or time, it is difficult to continuously authenticate a user (a person to be collated) at all times. Thus, when a user is intentionally replaced by another person after the authentication, since detecting the replacement is impossible, security level becomes low. Moreover, acoustic characteristics for identifying individual information need to be stored in a robust storage device in advance.

Therefore, in view of the aforementioned problems, the present invention aims to provide a personal authentication device capable of simply securing security with little psychological and physical burden of a user to be authenticated.

To solve the above problem, a personal authentication device according to first aspect of the present invention includes:
  a storage means for storing first identification information for identifying a user and second identification information for continuously identifying the user by a method other than identification;
  an analysis means for analyzing information inputted to a user and generating the first identification information;
  a transmission means for transmitting a first acoustic signal to a part of a head of the user;
  an observation means for observing a second acoustic signal that is an acoustic signal after the first acoustic signal propagates through the part of the head of the user;
  a calculation means for calculating acoustic characteristics from the first acoustic signal and the second acoustic signal;
  an extraction means for extracting an acoustic feature amount related to the user from the acoustic characteristics as second identification information; and
  a determination means for determining the user to be identical when first identification information registered in the storage means and the first identification information generated by the analysis means coincide with each other as a collation result and second identification information registered in the storage means and the second identification information extracted from the extraction means coincide with each other as a collation result.

A personal authentication method according to first aspect of the present invention includes:
  analyzing information inputted to a user and generating first identification information for identifying the user;
  transmitting a first acoustic signal to a part of a head of the user;
  observing a second acoustic signal that is an acoustic signal after the first acoustic signal propagates through the part of the head of the user;
  calculating acoustic characteristics from the first acoustic signal and the second acoustic signal;

extracting an acoustic feature amount related to the user from the acoustic characteristics as second identification information for continuously identifying the user; and determining the user to be identical when first identification information registered in a storage means in advance and the first identification information generated by the analysis means coincide with each other as a collation result and second identification information registered in the storage means and the second identification information extracted from the extraction means coincide with each other as a collation result.

A personal authentication program according to third aspect of the present invention causes a computer to perform:

analyzing information inputted to a user and generating first identification information for identifying the user;

transmitting a first acoustic signal to a part of a head of the user;

observing a second acoustic signal that is an acoustic signal after the first acoustic signal propagates through the part of the head of the user;

calculating acoustic characteristics from the first acoustic signal and the second acoustic signal;

extracting an acoustic feature amount related to the user from the acoustic characteristics as second identification information for continuously identifying the user; and determining the user to be identical when first identification information registered in a storage means in advance and the first identification information generated by the analysis means coincide with each other as a collation result and second identification information registered in the storage means and the second identification information extracted from the extraction means coincide with each other as a collation result.

The personal authentication program may be stored in a non-transitory storage medium.

Advantageous Effects of Invention

According to the present invention, it is possible to provide a personal authentication device capable of simply securing security with little psychological and physical burden of a user to be authenticated.

BRIEF DESCRIPTION OF DRAWINGS

FIG. 3 is a flowchart illustrating an example of an operation of a personal authentication device according to a first example embodiment of the present invention.

FIG. 4A is a graph illustrating an example of a transmitted acoustic signal.

FIG. 4B is a graph illustrating an example of an observed acoustic signal.

FIG. 5 is a graph illustrating an example of an impulse response as acoustic characteristics.

EXAMPLE EMBODIMENT

First Example Embodiment

In a first example embodiment of the present invention, identification (ID) information and password information are used in order to authenticate a user. As the ID information, there is information which rarely changes and enables high precision authentication at once although continuous (constant) authentication imposes an excessive burden on a user, for example, a feature amount of a fingerprint, a feature amount of an iris, or a text string arbitrarily specified by a user. As the password information, there is information which does not impose an excessive burden on a user in spite of constant authentication, for example, an external ear acoustic feature amount in a state of wearing a headphone and the like. By a combination thereof, it is possible to simply realize robust security.

(Personal Authentication Device)

Figure 1:
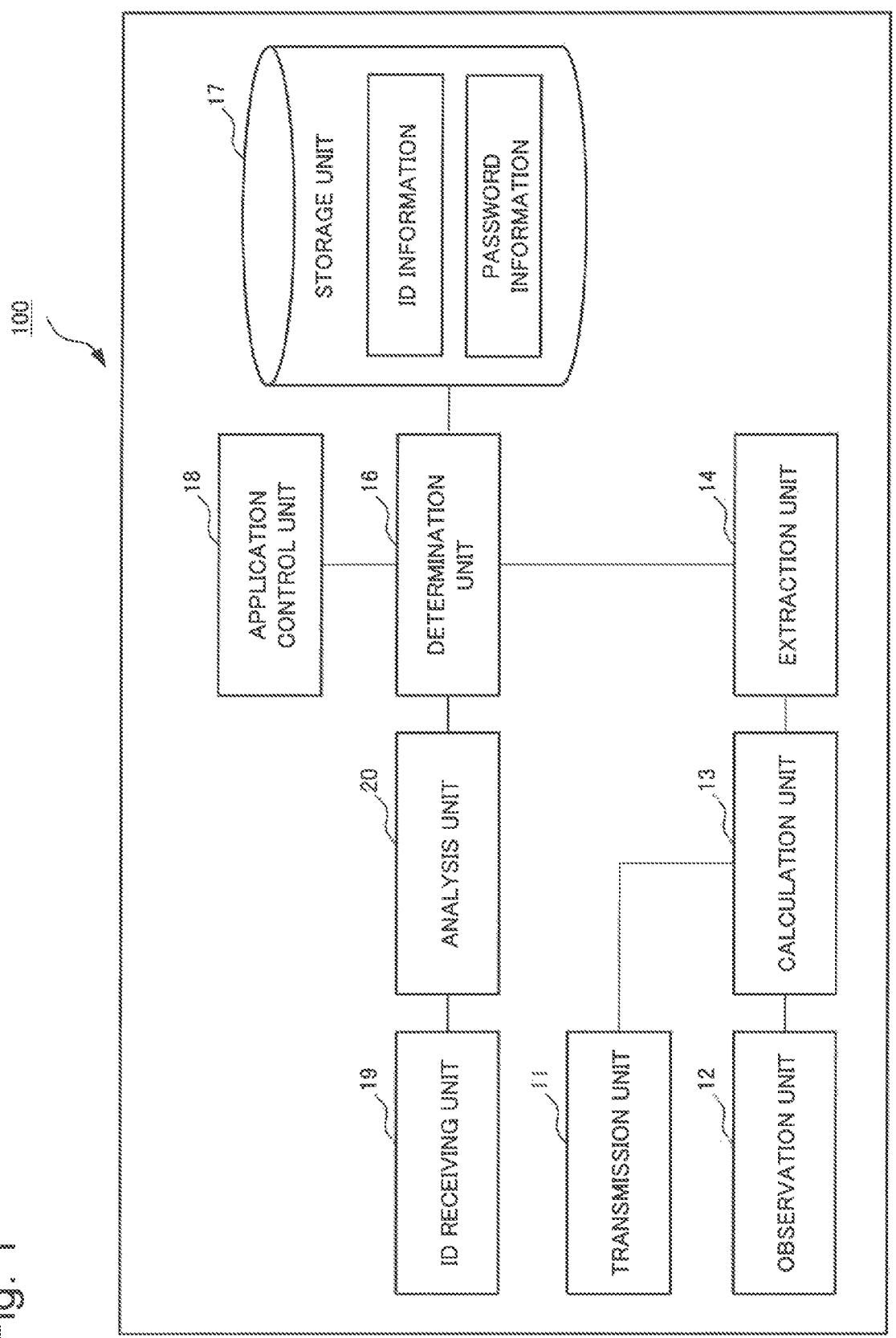
FIG. 1 is a block diagram illustrating a configuration example of a personal authentication device according to a first example embodiment of the present invention.

Personal authentication device 100 according to a first example embodiment of the present invention will be described with reference to the drawings. FIG. 1 is a block diagram illustrating a configuration example of personal authentication device 100 according to the first example embodiment. Personal authentication device 100 illustrated in FIG. 1 includes transmission unit 11, observation unit 12, calculation unit 13, extraction unit 14, determination unit 16, storage unit 17, application control unit 18, ID acquisition unit 19, and analysis unit 20.

Transmission unit 11 transmits an acoustic signal to a part of a user's head. The part of the head, to which the acoustic signal is transmitted, is more specifically an area where a cavity has been formed in the head, and may be at least a part of an area where it is possible to mount or approximate an ornament or a device for producing a sound effect.

Observation unit 12 observes an acoustic signal after the acoustic signal transmitted from transmission unit 11 propagates through the part of the user's head. Furthermore, the part of the head serving as the propagation path of the acoustic signal may be more specifically at least a part of a skull, a brain, and a sensory organ constituting the head, and a cavity among them.

Calculation unit 13 calculates acoustic characteristics of the acoustic signal propagating through the part of the user's head on the basis of the acoustic signal transmitted from transmission unit 11 and the acoustic signal observed by observation unit 12.

Extraction unit 14 extracts a feature amount related to a user to be authenticated (an authentication target user) from the calculated acoustic characteristics. The extraction of the feature amount may be performed by a predetermined arithmetic operation.

Storage unit 17 stores ID information and password information of a user. The ID information is identification information which rarely changes and enables high precision authentication at once, and for example, includes fingerprint information (a fingerprint feature amount) of the user, iris information (an iris feature amount) of the user, or a text string arbitrarily specified by the user. The password information is information capable of continuously identifying the user other than the ID information, and for example, in the present example embodiment, external ear authentication information (an acoustic feature amount) of the user is used.

ID receiving unit 19 receives input of information as an ID from the user. The reception is performed via an input device such as a keyboard and a scanner. For example, when a fingerprint feature amount is employed as the ID information, a fingerprint image of the user is read from the scanner.

Analysis unit 20 analyzes the information acquired by ID receiving unit 19 into information compatible with the ID information stored in storage unit 17, and outputs an analysis result. For example, in the case of a fingerprint, analysis unit 20 analyzes a read fingerprint image and outputs a feature amount of the fingerprint as an analysis result.

Determination unit 16 collates the acoustic feature amount (password information) obtained by extraction unit 14 with the acoustic feature amount stored in storage unit 17, and determines whether these feature amounts coincide with each other. Moreover, determination unit 16 collates the fingerprint feature amount (ID information) obtained by analysis unit 20 with the fingerprint feature amount stored in storage unit 17, and determines whether these feature amounts coincide with each other. When there is coincidence in the ID information and the password information, determination unit 16 determines that a user to be authenticated is a registered user (user identity) and outputs a determination result. When there is no coincidence in at least one of the ID information and the password information, determination unit 16 determines that the user to be authenticated is not the registered user and outputs a determination result.

Application control unit 18 controls an application program. For example, when the determination result of determination unit 16 is the registered user, application control unit 18 controls an application to be started or to be maintained in a startup state, and when the determination result is not the registered user, application control unit 18 controls an application not to be started or an application being started to be ended.

Herein, the application in the present example embodiment is an application that should identify personal information (a name and the like) of a user using the application and should prohibit the application from being used by others, or an application intended to detect the absence of a user. For example, the application relates to an application which is used in work related to safety of a country or a region (for example, a police, a security guard, or an army) and should prevent impersonation, an application which is used in wireless communication or wireless calls that transmits confidential content and should prevent eavesdropping, and an application which should authenticate a worker who is working at a medical site or a construction site.

Figure 2:
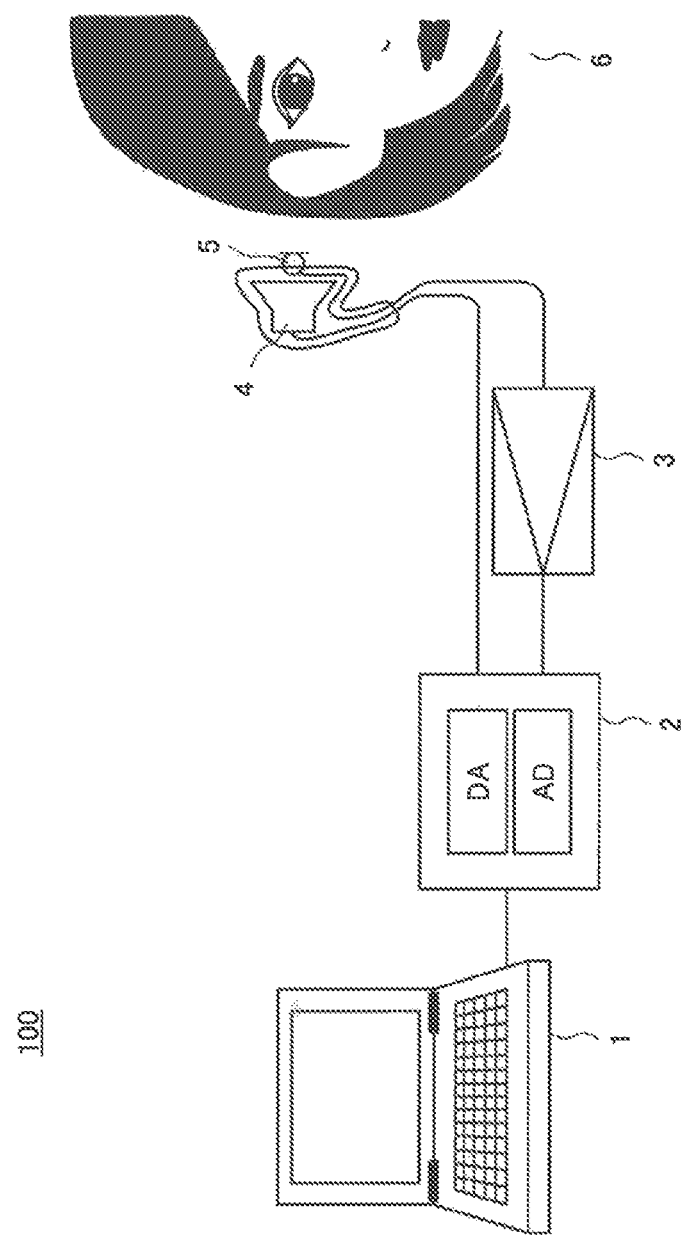
FIG. 2 is a configuration diagram illustrating a specific hardware configuration example of a personal authentication device according to a first example embodiment of the present invention.

FIG. 2 is a configuration diagram illustrating a specific hardware configuration example for implementing personal authentication device 100 of the present example embodiment illustrated in FIG. 1. Personal authentication device 100, for example, includes information processing device 1, sound processor 2, microphone amplifier 3, earphone 4, and microphone 5. Specifically, information processing device 1 is a smart phone, a tablet terminal, or a personal computer. Reference numeral 6 denotes a user to be recognized.

Password information (acoustic feature amount) is described later. Sound transmitted from information processing device 1 is subjected to D/A (digital/analog) conversion in sound processor 2 and is delivered to earphone 4. Earphone 4 includes microphone 5. Earphone 4 is mounted on or inserted into a user's ear, sound produced by microphone 5 is echoed in the ear, and earphone 4 collects the echo sound. The collected echo sound is amplified by microphone amplifier 3, is subjected to A/D (analog/digital) conversion in sound processor 2, and is transmitted to information processing device 1.

In the hardware configuration example illustrated in FIG. 2, earphone 4 is an example of transmission unit 11. Furthermore, microphone 5, sound processor 2, and microphone amplifier 3 are an example of observation unit 12. As illustrated in FIG. 2, it is desired that microphone 5 and earphone 4 are integrated such that their relative positional relation does not change. However, when the relative positional relation therebetween does not change significantly, the present invention is not limited thereto. Furthermore, as an example of earphone 4 and microphone 5, a microphone-integrated earphone, in which they are inserted into the entrance of an ear canal, is used; however, as a practical example of both, a microphone may be set on a headphone that covers the auricle. Furthermore, as another practical example of both, a microphone may be installed in a handset part of a telephone. In addition, an acoustic signal transmitted by an earphone installed at the entrance of the ear canal of the left ear may be observed with a microphone installed at the entrance of the ear canal of the right ear, or vice versa. The acoustic feature quantity may be extracted from both ears or from one of the left and right ears.

ID receiving unit 19, analysis unit 20, calculation unit 13, extraction unit 14, determination unit 16, and application control unit 18 are respectively implemented by a central processing unit (CPU) and a memory operating according to a program in information processing device 1.

Furthermore, storage unit 17 is implemented by a recording medium such as a hard disk in information processing device 1. An input device (a scanner, a keyboard and the like) for inputting an ID is necessary in ID receiving unit 19, but it is assumed that these are provided in information processing device 1. When a necessary input device is not provided in information processing device 1, an external input device may be connected to information processing device 1.

(Operation of Personal Authentication Device)

Next, an example of the operation of personal authentication device 100 in the present example embodiment will be described with reference to the flowchart illustrated in FIG. 3. In the following example embodiment, it is assumed that ID information (a text string and biometric information such as a fingerprint feature amount) and password information (an acoustic feature amount) of a user are stored in storage unit 17 in advance by a system administrator.

In step S100, ID receiving unit 19 receives ID information. In the present example embodiment, a description will be given on the assumption that a user's fingerprint is the ID information. A fingerprint image read from a screen of information processing device 1 is transmitted to analysis unit 20. Analysis unit 20 analyzes the fingerprint image and outputs a fingerprint feature amount as an analysis result.

In step S105, determination unit 16 determines whether the analysis result coincides with the ID information stored in storage unit 17. When the analysis result coincides with the ID information, the procedure proceeds to step S110, and when the analysis result does not coincide with the ID information, the procedure proceeds to step S210.

That is, in step S110, when the user wears earphone 4 in his/her ear, transmission unit 11 transmits an acoustic signal toward a part of a head of the user to be authenticated. For example, in step S110, earphone 4 transmits an acoustic signal toward an ear canal from the entrance of the ear canal. As the acoustic signal, a method using, such as, an M-sequence signal (maximal length sequence), a time stretched pulse (TSP) signal a widely used for measuring an impulse response is considered.

FIG. 4A is a graph illustrating an example of the acoustic signal transmitted by transmission unit 11. In the graph of FIG. 4A, a horizontal axis denotes time t and a vertical axis denotes a signal value x(t) of the acoustic signal transmitted at time t. Hereinafter, the acoustic signal transmitted by transmission unit 11 may be called a transmitted acoustic signal.

In step S120, observation unit 12 observes an acoustic signal after the acoustic signal transmitted from transmission unit 11 in step S110 propagates through the part of the user's head. For example, in step S120, microphone 5 detects the acoustic signal propagated from earphone 4. The detected acoustic signal is amplified by microphone amplifier 3, is subjected to A/D conversion in sound processor 2, and is transmitted to information processing device 1.

FIG. 4B is a graph illustrating an example of the acoustic signal observed by observation unit 12. In the graph of FIG. 4B, a horizontal axis denotes time t and a vertical axis denotes a signal value y(t) of the acoustic signal observed at time t. Hereinafter, the acoustic signal observed by observation unit 12 may be called an observed acoustic signal.

In step S130, calculation unit 13 calculates acoustic characteristics of the part of the user's head from a change in the transmitted acoustic signal and the observed acoustic signal. The acoustic characteristics include, such as, an impulse response, a transfer function obtained by performing Fourier transform or Laplace transform on the impulse response. The acoustic characteristics, for example, include information regarding how the acoustic signal is reflected and/or attenuated in a living body. For example, when earphone 4 and microphone 5 are installed at the entrance of an ear canal and acoustic characteristics that reflect in the ear canal are calculated by calculation unit 13, an ear canal impulse response or an ear canal transfer function may be used as the acoustic characteristics.

FIG. 5 is a graph illustrating an example of the impulse response as the acoustic characteristics calculated by calculation unit 13. In the graph of FIG. 5, a horizontal axis denotes time t and a vertical axis denotes a value g(t) of an impulse response of an acoustic signal observed at time t.

Among the signal value x(t) of the transmitted acoustic signal, the signal value y(t) of the observed acoustic signal, and the value g(t) of the impulse response, there is a relation expressed by the following Formula (1).

[Formula 1]

$$y(t) = \int_0^t x(\tau) g(t-\tau) d\tau \quad (1)$$

Furthermore, among X(f), Y(f), and G(f) obtained by respectively performing Fourier transform on x(t), y(t), and g(t), there is a relation expressed by the following Formula (2). In Formula (2) below, f denotes a frequency band. Furthermore, G denotes a transfer function.

$$Y(f) = G(f)X(f) \quad (2)$$

In step S140, extraction unit 14 extracts a feature amount from the acoustic characteristics calculated by calculation unit 13. As the feature amount, the impulse response or the transfer function may be used as is. That is, extraction unit 14 uses values of each time of the impulse response as the acoustic characteristics or values of each frequency of the transfer function as the feature amount. Furthermore, it is considered to use a feature amount obtained by performing main component analysis and dimensional compression on the impulse response or the transfer function as the acoustic characteristics, or to use mel-frequency cepstrum coefficients (mfcc) disclosed in NPL 1 as a feature amount.

In step S180, determination unit 16 collates the acoustic feature amount obtained by extraction unit 14 with the acoustic feature amount of a registered user stored in storage unit 17.

In step S190, when the feature amounts coincide with each other as the collation result and it is determined that a user to be authenticated corresponds to a registered user, the procedure proceeds to step S200. When the feature amounts do not coincide with each other as the collation result and it is determined that the user to be authenticated does not correspond to the registered user, the procedure proceeds to step S210. This determination corresponds to one-to-one authentication.

In the one-to-one authentication, feature amounts of a user to be authenticated and a registered user are collated with each other in a one-to-one manner. In such a case, a registered user, for which collation is to be performed, may be designated in advance with a user identification (ID). As a collation method, for example, identification unit 16 may calculate a distance between feature amounts, determine that they are the same person when the distance is smaller than a threshold value, and determine that they are different persons when the distance is larger than the threshold value. As a distance measure, such as the Euclid distance or a cosine distance is considered. However, other distances may be used.

Furthermore, in the above, an example, in which a feature amount stored in advance is stored in storage unit 17, has been described; however, storage unit 17 may store a statistical model instead of the feature amount. The statistical model may be a mean value and a variance value obtained by acquiring a feature amount multiple times for one person, or a relational expression calculated using these values. Alternatively, there are, for example, a Gaussian mixture model (GMM), a support vector machine (SVM), a model using a neutral network, as disclosed in PTL 1.

In step S200, determination unit 16 waits for the passage of a predetermined time (for example, one second). Thereafter, in step S170, application control unit 18 starts an application. Alternatively, when an application is being executed, application control unit 18 maintains the execution state and returns the procedure to step S110.

In step S210, application control unit 18, for example, ends an application program being used such that the application is not used by a user who is not a registered user. In such a case, storage unit 17 may be allowed to store an acoustic feature amount of an unauthorized user who is not a registered user.

In addition, application control unit 18 may end an application program for a service according to a request from a registered user. Furthermore, when a registered user detaches earphone 4 from his/her ear and thus extraction unit 14 is not able to completely acquire a feature amount (echo sound), application control unit 18 may end the application program for a service. In such a case, determination unit 16 may not immediately but after several times of collation, notify application control unit 18 of a collation result and service stop, after it is found that some reason prevent identification unit 16 from acquiring a feature amount, after several tries.

Thus, the operation of personal authentication device 100 according to the first example embodiment is ended.

According to the first example embodiment of the present invention, it is possible to provide a personal authentication device capable of simply securing security with little psychological and physical burden of a user to be authenticated. This is because the first authentication, which is performed only when an application is started, and the second authentication, which is performed continuously when an application is executed, are performed in keeping with each other.

According to the first example embodiment of the present invention, as second authentication, it is possible to provide a personal authentication device capable of simply securing security with little psychological and physical burden of a user to be authenticated. In the present example embodiment, personal authentication is performed using a characteristic in which acoustic characteristics of an acoustic signal propagating through a part of a user's head are different for each individual. Since the acoustic characteristics propagating through the part of the user's head are internal characteristics of a living body differently from characteristics observable from an exterior such as a face and a fingerprint, the risk of leakage is low and theft is difficult. Furthermore, in order to know acoustic characteristics, since both the transmitted acoustic signal and the observed acoustic signal are necessary, there is little risk of being acquired and forged by eavesdropping. Furthermore, since an operation to be performed by a user to be authenticated is to wear a headphone or an earphone with an embedded microphone or hold a cellular phone with a microphone embedded in a receiving part to an ear, psychological and physical burden of a user is small. Furthermore, when the personal authentication method of the present example embodiment is used in combination with music distribution, a transceiver, or an information distribution device that transmits voice such as communication, it is possible to provide a user with personal authentication without any additional physical and mental burden.

Furthermore, the acoustic characteristics can be acquired in a short period, such as about one second, and it is possible to keep authenticating a user at all times while a service is being provided. Therefore, as collated with a case where authentication is performed once at the beginning or immediately before receiving any service, when there is an illegal act such as alternation (impersonation) to another person after the authentication, it is possible to detect the illegal act.

Second Example Embodiment

In the first example embodiment of the present invention, a user is identified using two types of identification information, but it is assumed that the identification information is stored in the storage unit in advance. In the second example embodiment of the present invention, it is assumed that one (ID information) of two pieces of identification information is fixed in principle, but the other one (password information) is variable and is newly registered whenever an application is executed even in the case of the same user. In this way, it is possible to achieve higher security performance.

(Personal Authentication Device)

Figure 6:
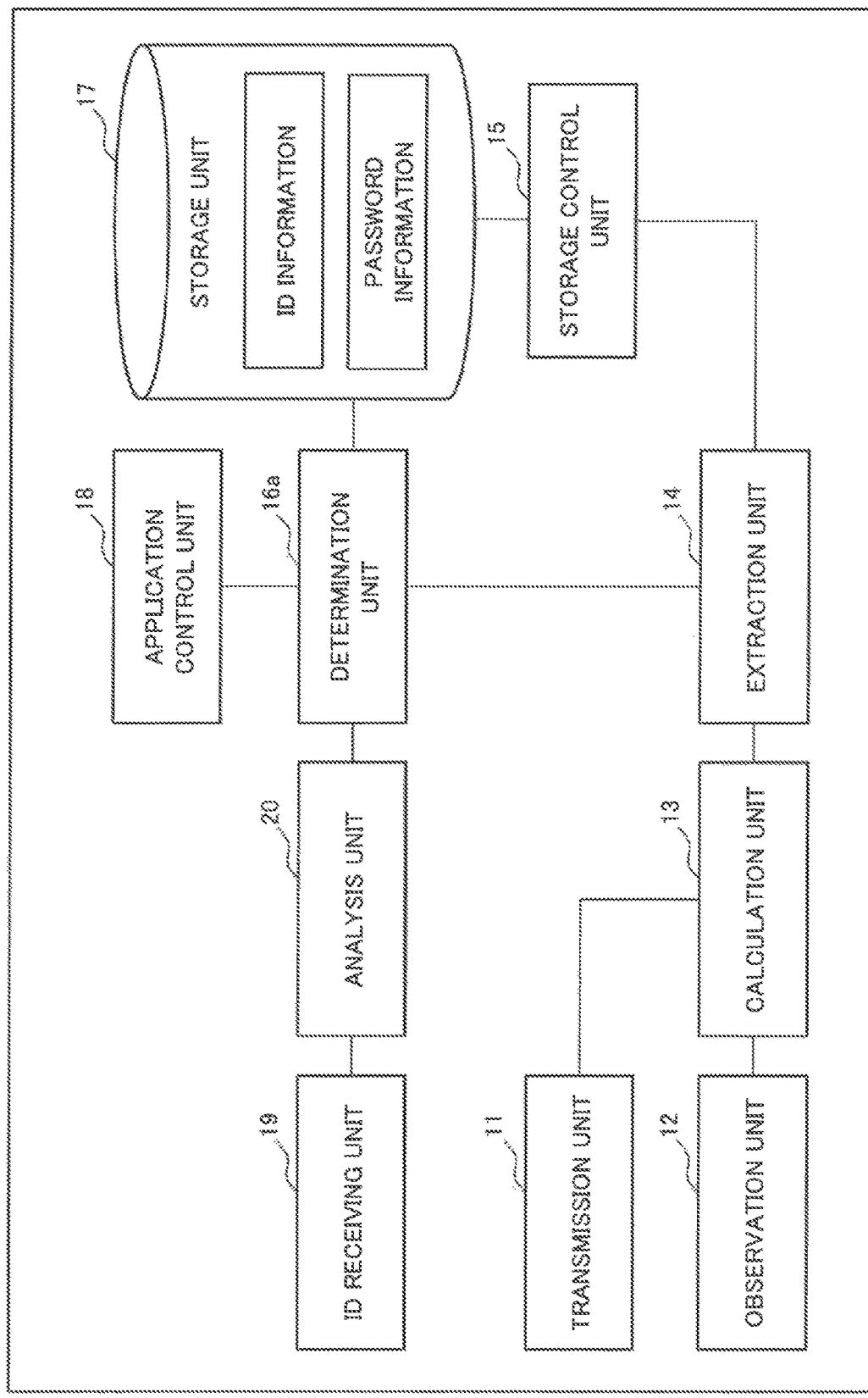
FIG. 6 is a block diagram illustrating a configuration example of a personal authentication device according to a second example embodiment of the present invention.

Personal authentication device 200 according to the second example embodiment of the present invention will be described with reference to the drawings. FIG. 6 is a block diagram illustrating a configuration example of personal authentication device 200 according to the second example embodiment. Personal authentication device 200 illustrated in FIG. 6 includes transmission unit 11, observation unit 12, calculation unit 13, extraction unit 14, storage control unit 15, determination unit 16a, storage unit 17, application control unit 18, ID receiving unit 19, and analysis unit 20.

Storage unit 17 stores ID information and password information of a user. The password information is information capable of continuously identifying the user other than the ID information, and for example, in the present example embodiment, external ear authentication information (an acoustic feature amount) of the user is used. In the present example embodiment, whenever an application is started, the password information is updated and stored. The ID information is also stored in storage unit 17, but a system administrator and the like, other than a user to be authenticated, register ID information related to the user and it is assumed that the user can change ID information only via the system administrator.

Storage control unit 15 stores an acoustic feature amount (password information) of an authentication target user in storage unit 17 at the time of registration of the user when an application is started (hereinafter, this may be described as first registration). Moreover, when each application is stopped, storage control unit 15 deletes the acoustic feature amount of the authentication target user from storage unit 17. That is, the acoustic feature amount serving as a password is stored and deleted whenever an application is executed even in the case of the same user. As described above, a so-called one-time password method, in which a password is changed in a short period of time, is employed. Accordingly, it is not necessary to store an acoustic feature amount in storage unit 17 in advance. Moreover, an acoustic feature amount is stored in storage unit 17 whenever an application is executed, so that it is possible to secure high security.

Storage unit 17 stores the feature amount related to the authentication target user at the time of the first registration of the user. Hereinafter, a user, whose feature amount is stored in storage unit 17, may be called a registered user.

Determination unit 16a collates the acoustic feature amount (password information) obtained by extraction unit 14 with the acoustic feature amount stored in storage unit 17 at the time of the first registration, and determines whether these feature amounts coincide with each other. Moreover, determination unit 16a collates the fingerprint feature amount (ID information) obtained by analysis unit 20 with the fingerprint feature amount stored in storage unit 17, and determines whether these feature amounts coincide with each other.

The extraction of the acoustic feature amount by extraction unit 14 may be performed from both ears or from the right or left ear only. In the present example embodiment, during a predetermined operation requiring authentication, a user is required to wear earphone 4 at all times. Thus, in the case of a predetermined operation over a long period of time, it is also assumed that a user experiences pain or a sense of discomfort in the ear. In such a case, the user may appropriately change an ear with earphone 4 to the other ear. It should be noted that when changing an ear to be authenticated, a first registration operation to be described later is necessary again.

ID receiving unit 19, analysis unit 20, calculation unit 13, extraction unit 14, storage control unit 15, determination unit 16a, and, application control unit 18 are respectively implemented by a central processing unit (CPU) and a memory operating according to a program in information processing device 1. Furthermore, storage unit 17 is implemented by a recording medium such as a hard disk in information processing device 1.

The others are the same as those of the first example embodiment.

(Operation of Personal Authentication Device)

Figure 7:
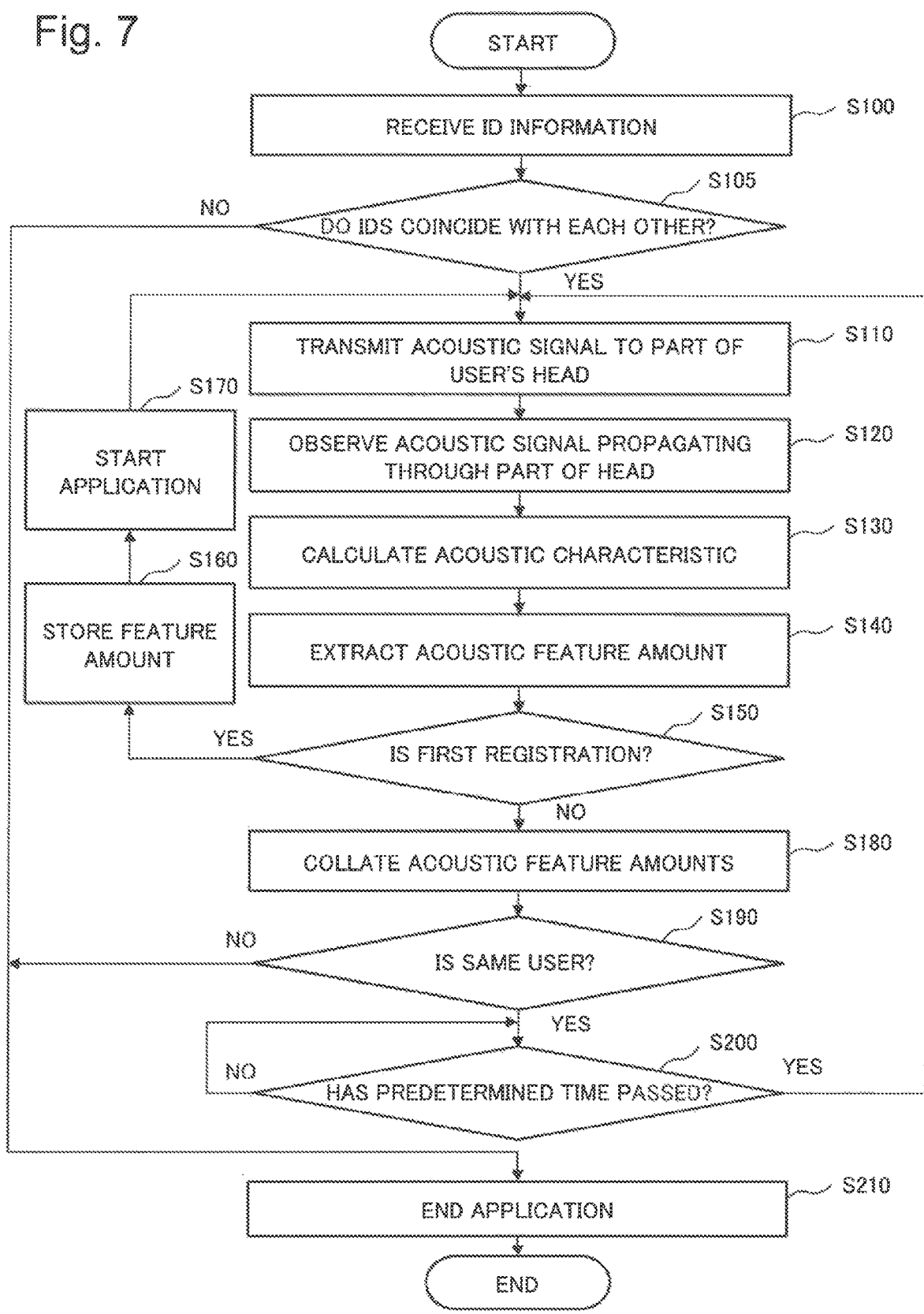
FIG. 7 is a flowchart illustrating an example of an operation of a personal authentication device according to a second example embodiment of the present invention.

Next, an example of the operation of personal authentication device 200 in the present example embodiment will be described with reference to the flowchart illustrated in FIG. 7. In the following example embodiment, ID information (a text string and biometric information such as a fingerprint feature amount) of a user are stored in storage unit 17 in advance by a system administrator.

Steps S100, S105, S110 to S140 are the same as those of the first example embodiment (FIG. 3).

In step S150, determination unit 16a determines whether the extraction of an acoustic feature amount this time is the first extraction for a user. As a specific example, the determination unit 16a includes a counter memory for counting the number of extractions or searches whether data of an acoustic feature amount (password information) exists in storage unit 17, thereby performing the above determination. When it is determined as the first extraction, that is, the first registration, the procedure proceeds to step S160, and when it is not determined as the first registration (the second time or more), the procedure proceeds to step S180.

When it is the first registration, storage control unit 15 stores the acoustic feature amount extracted in extraction unit 14 in storage unit 17 in step S160. In step S170, when it is detected that the acoustic feature amount is present in storage unit 17, application control unit 18 starts an application program.

When it is not the first registration, determination unit 16a collates the acoustic feature amount obtained by extraction unit 14 with the acoustic feature amount of a registered user stored in storage unit 17 in step S180.

In step S190, when the acoustic feature amounts coincide with each other as the collation result and it is determined that a user to be authenticated corresponds to a registered user, the procedure proceeds to step S200. When the acoustic feature amounts do not coincide with each other as the collation result and it is determined that the user to be authenticated does not correspond to the registered user, the procedure proceeds to step S210.

In step S200, determination unit 16a waits for the passage of a predetermined time (for example, one second) and returns the procedure to step S110.

In step S210, application control unit 18, for example, ends an application program being used such that the application is not used by a user who is not a registered user. In such a case, storage control unit 15 may allow storage unit 17 to store a feature amount of an unauthorized user who is not a registered user. Before and after an application is ended, application control unit 18 instructs storage control unit 15 to erase data of the feature amount of the registered user in storage unit 17. Storage control unit 15 erases the data of the feature amount of the registered user whenever the application program is ended.

Thus, the operation of personal authentication device 200 according to the second example embodiment is ended.

According to the second example embodiment of the present invention, it is possible to provide a personal authentication device with little psychological and physical burden of a user to be authenticated, which can simply secure security.

In the second example embodiment, in addition to the effects of the first example embodiment, whenever an application is started, acoustic feature amount data of a user is registered in storage unit 17, and whenever the application is ended, the acoustic feature amount data registered in storage unit 17 is erased. In this way, since acoustic feature amount data used as a password is collated only for a short period of time (only a one-time application use time), it is possible to simply secure high security.

Moreover, even though a user with one-ear authentication has a sense of discomfort to an ear used for authentication due to the long-time use of an application and desires to switch the authentication subject to the other ear, it is possible to easily switch the ear to be authenticated by inputting ID information (an acoustic feature amount) to information processing device 1 again.

Third Example Embodiment

Figure 8:
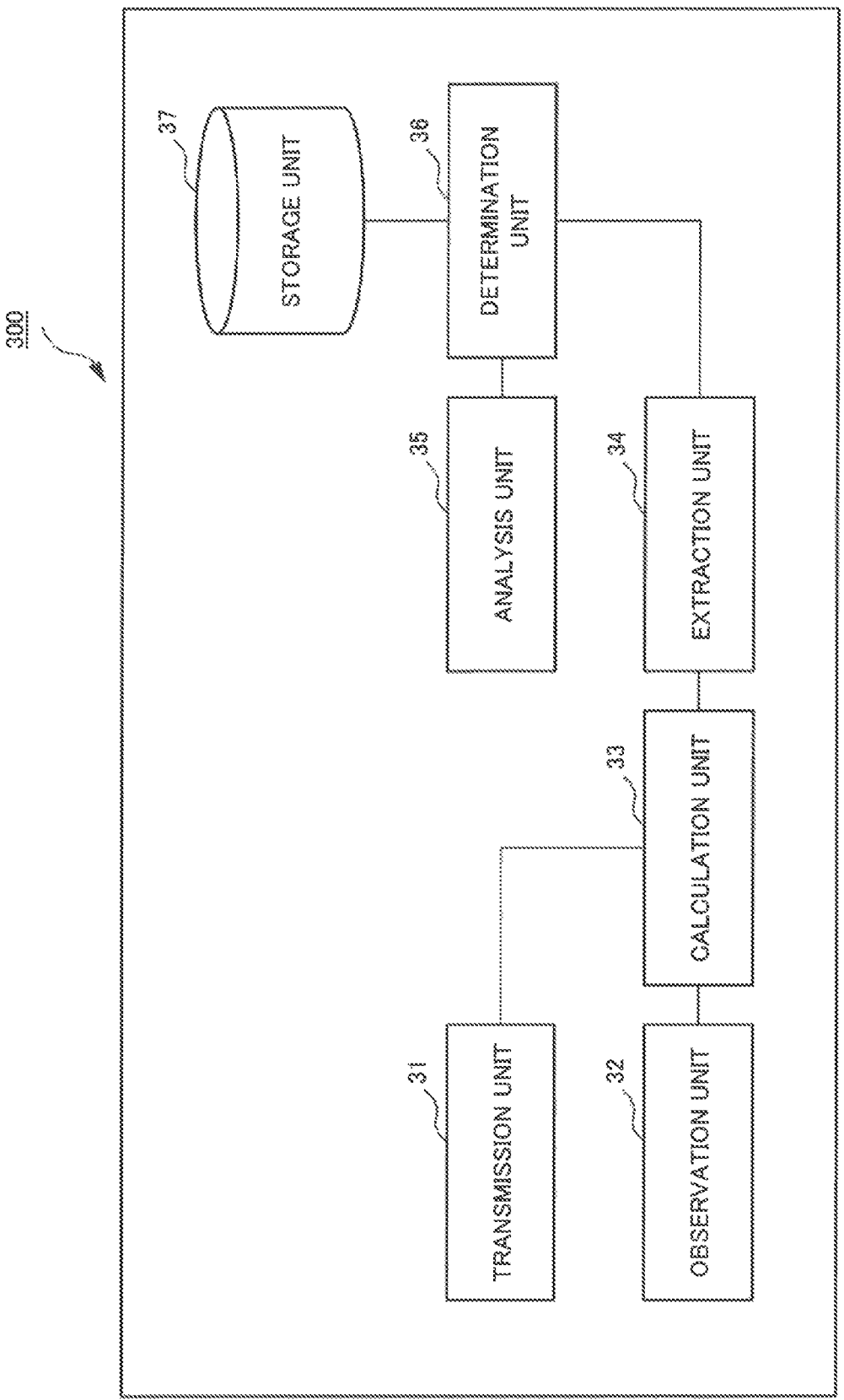
FIG. 8 is a block diagram illustrating a configuration example of a personal authentication device according to a third example embodiment of the present invention.
Figure 9:
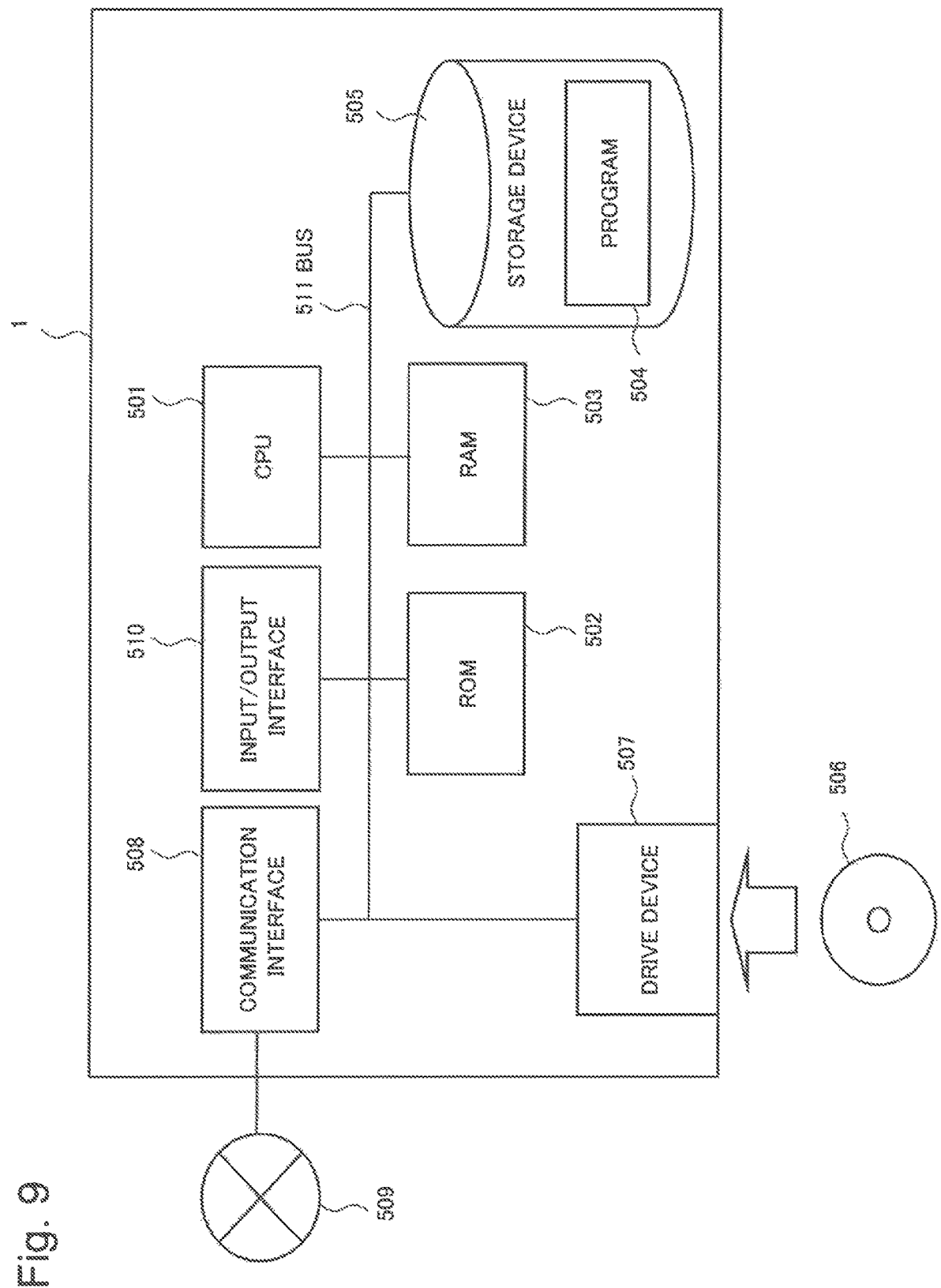
FIG. 9 is a configuration example of an information processing device for embodying each example embodiment according to the present invention.

Personal authentication device 300 according to a third example embodiment of the present invention includes transmission unit 31, observation unit 32, calculation unit 33, extraction unit 34, analysis unit 35, determination unit 36, and storage unit 37 as illustrated in FIG. 8. An example of personal authentication device 300 illustrated in FIG. 8 may be personal authentication device 100 of the first example embodiment illustrated in FIG. 1. Another example of personal authentication device 300 may be personal authentication device 200 of the second example embodiment illustrated in FIG. 6.

Storage unit 37 is designed to be able to store first identification information (ID information) for identifying a user and second identification information (password information) for continuously identifying the user by a method other than identification.

Analysis unit 35 analyzes information inputted to a user and generates the first identification information.

Transmission unit 31 transmits a first acoustic signal to a part of a user's head.

Observation unit 32 observes a second acoustic signal that is an acoustic signal after the first acoustic signal propagates through the part of the user's head.

Calculation unit 33 calculates acoustic characteristics from the first acoustic signal and the second acoustic signal.

Extraction unit 34 extracts an acoustic feature amount related to the user from the acoustic characteristics as second identification information.

Determination unit 36 determines the user to be identical when first identification information registered in storage unit 37 and the first identification information generated by analysis unit 35 coincide with each other as a collation result and second identification information registered in storage unit 37 and the second identification information extracted from extraction unit 34 coincide with each other as a collation result.

According to the third example embodiment of the present invention, it is possible to provide a personal authentication with little psychological and/or physical burden of a user to be authenticated and with high security performance. The reason for this is because determination unit 36 determines identity of a user based on first identification information (ID information) for identifying the user and second identification information (password information) for identifying the user by a method other than identification. In this way, the user is subjected to ID authentication when an application is executed then is unconsciously subjected to password authentication at all times in a state of simply wearing an earphone and the like, so that security performance becomes high and continuous personal authentication becomes possible.

(Configuration of Information Processing Device)

In the aforementioned each example embodiment of the present invention, respective elements of respective personal authentication devices illustrated in FIG. 1, FIG. 6, and FIG. 8 illustrate blocks of a functional unit. Some or all of respective elements of the personal authentication devices, for example, are realized using an arbitrary combination of information processing device 1 as illustrated in FIG. 10 and a program. Information processing device 1 includes the following elements as an example.

Central processing unit (CPU) 501
Read only memory (ROM) 502
Random access memory (RAM) 503
Program 504 loaded on RAM 503
Storage device 505 storing program 504
Drive device 507 for performing reading and writing of recording medium 506
Communication interface 508 connected to communication network 509
Input/output interface 510 for performing input/output of data
Bus 511 connecting each element Respective elements of the personal authentication device in each example embodiment of the present invention are implemented when CPU 501 acquires and executes program 504 for performing functions of the elements. Program 504 for performing the functions of the elements of the personal authentication device, for example, is stored in storage device 505 or RAM 503 in advance and is read by CPU 501 when necessary. It should be noted that program 504 may be supplied to CPU 501 via communication network 509, or drive device 507 may read program 504 stored in recording medium 506 in advance and supply CPU 501 with read program 504.

There are various modification examples in the implementation method of each device. For example, the personal authentication device may be implemented by an arbitrary combination of different information processing devices and programs for each element. Furthermore, a plurality of elements included in the personal authentication device may be implemented by an arbitrary combination of one information processing device 1 and a program.

Furthermore, some or all of respective elements of respective personal authentication devices are implemented by other general-purpose or dedicated circuits, processors or a combination thereof. These may also be configured by a single chip, or by a plurality of chips connected via a bus.

Some or all of respective elements of respective personal authentication devices may be implemented by a combination of the aforementioned circuits and a program.

When some or all of respective elements of respective personal authentication devices are implemented by a plurality of information processing devices, circuits, the plurality of information processing devices, circuits may be arranged in a concentrated manner or arranged in a distributed manner. For example, the information processing devices, circuits may be implemented as a form in which a client and server system, a cloud computing system are connected to one another via a communication network.

Some or all of the aforementioned example embodiments are also described in the following Supplementary Notes; however, the present invention is not limited thereto.

[Supplementary Note 1]

A personal authentication device comprising:
a storage means for storing first identification information for identifying a user and second identification information for continuously identifying the user by a method other than identification;
an analysis means for analyzing information inputted to a user and generating the first identification information;
a transmission means for transmitting a first acoustic signal to a part of a head of the user;
an observation means for observing a second acoustic signal that is an acoustic signal after the first acoustic signal propagates through the part of the head of the user;
a calculation means for calculating acoustic characteristics from the first acoustic signal and the second acoustic signal;
an extraction means for extracting an acoustic feature amount related to the user from the acoustic characteristics as second identification information; and
a determination means for determining the user to be identical when first identification information registered in the storage means and the first identification information generated by the analysis means coincide with each other as a collation result and second identification information registered in the storage means and the second identification information extracted from the extraction means coincide with each other as a collation result.

[Supplementary Note 2]

The personal authentication device according to Supplementary Note 1, further comprising:
a storage control means for deleting the second identification information registered in the storage means when the collation result of the second identification information does not indicate coincidence and the user is not determined to be identical.

[Supplementary Note 3]

The personal authentication device according to Supplementary Note 1 or 2, wherein, when the second identification information is not stored in the storage means, the storage control means stores the extracted second identification information in the storage means.

[Supplementary Note 4]

The personal authentication device according to Supplementary Note 1, wherein, when the user is determined to be identical, the transmission means transmits the first acoustic signal every predetermined interval.

[Supplementary Note 5]

The personal authentication device according to any one of Supplementary Notes 1 to 4, further comprising:
an application control means for allowing the user to execute an application program when the user is determined to be identical.

[Supplementary Note 6]

A personal authentication method comprising:
analyzing information inputted to a user and generating first identification information for identifying the user;
transmitting a first acoustic signal to a part of a head of the user;
observing a second acoustic signal that is an acoustic signal after the first acoustic signal propagates through the part of the head of the user;
calculating acoustic characteristics from the first acoustic signal and the second acoustic signal;
extracting an acoustic feature amount related to the user from the acoustic characteristics as second identification information for continuously identifying the user; and determining the user to be identical when first identification information registered in a storage means in advance and the first identification information generated by the analysis means coincide with each other as a collation result and second identification information registered in the storage means and the second identification information extracted from the extraction means coincide with each other as a collation result.

[Supplementary Note 7]

The personal authentication method according to Supplementary Note 6, further comprising:
deleting the second identification information registered in the storage means when the collation result of the second identification information does not indicate coincidence and the user is not determined to be identical.

[Supplementary Note 8]

The personal authentication method according to Supplementary Note 6 or 7, wherein, when the second identification information is not stored in the storage means, the extracted second identification information is stored in the storage means.

[Supplementary Note 9]

The personal authentication method according to Supplementary Note 6, wherein, when the user is determined to be identical, the first acoustic signal is transmitted every predetermined interval.

[Supplementary Note 10]

The personal authentication method according to any one of Supplementary Notes 6 to 9, further comprising:
allowing the user to execute an application program when the user is determined to be identical.

[Supplementary Note 11]

A recording medium stored with a personal authentication program causing a computer to perform:
analyzing information inputted to a user and generating first identification information for identifying the user;
transmitting a first acoustic signal to a part of a head of the user;
observing a second acoustic signal that is an acoustic signal after the first acoustic signal propagates through the part of the head of the user;
calculating acoustic characteristics from the first acoustic signal and the second acoustic signal;
extracting an acoustic feature amount related to the user from the acoustic characteristics as second identification information for continuously identifying the user; and
determining the user to be identical when first identification information registered in a storage means in advance and the first identification information generated by the analysis means coincide with each other as a collation result and second identification information registered in the storage means and the second identification information extracted from the extraction means coincide with each other as a collation result.

[Supplementary Note 12]

The recording medium according to Supplementary Note 11, further comprising:
deleting the second identification information registered in the storage means when the collation result of the second identification information does not indicate coincidence and the user is not determined to be identical.

[Supplementary Note 13]

The recording medium according to Supplementary Note 11 or 12, wherein, when the second identification information is not stored in the storage means, the extracted second identification information is stored in the storage means.

[Supplementary Note 14]

The recording medium according to Supplementary Note 11, wherein, when the user is determined to be identical, the first acoustic signal is transmitted every predetermined interval.

[Supplementary Note 15]

The recording medium according to any one of Supplementary Notes 11 to 14, further comprising:
allowing the user to execute an application program when the user is determined to be identical.

So far, the present invention has been described with reference to the present example embodiments and the examples; however, the present invention is not limited to the aforementioned example embodiments and examples. Various modifications which can be understood by a person skilled in the art can be made in the configuration and details of the present invention within the scope of the present invention.

REFERENCE SIGNS LIST 1 information processing device
2 sound processor
3 microphone amplifier
4 earphone
5 microphone
6 user
11 transmission unit
12 observation unit
13 calculation unit
14 extraction unit
15 storage control unit
16 determination unit
16a determination unit
17 storage unit
18 application control unit
28 application control unit
31 transmission unit
32 observation unit
33 calculation unit
34 extraction unit
35 storage control unit
36 determination unit
37 storage unit
100 personal authentication device
200 personal authentication device
300 personal authentication device
500 information processing device
501 CPU
503 RAM
504 program
505 storage device
506 recording medium
507 drive device
508 communication interface
509 communication network
510 input/output interface
511 bus

The invention claimed is:

1. A personal authentication method performed by a computer and comprising:
collating first biological information of a user with first registered biological information, the first biological information indicating a feature amount related to at least one of a fingerprint, an iris, a face, a voice, and a vein of the user;

allowing an application to execute based on a collating result related to the first biological information;

acquiring second biological information when the application executes, the second biological information being an external ear acoustic feature amount, by:
outputting a first signal to a device worn by the user, the first signal having a predetermined frequency;
receiving a second signal echoed in a part of body of the user; and
calculating the second biological information based on the second signal; and performing a predetermined action of the application based on a status of the second biological information acquisition.

2. The personal authentication method according to claim 1, further comprising:
terminating the application in response to failing to acquire the second biological information.

3. The personal authentication method according to claim 1, further comprising:
collating the second biological information with second registered biological information; and
identifying an individual based on the collating result related to the first biological information and a collating result related to the second biological information.

4. A personal authentication device comprising:
one or more memories storing instructions, first registered identification information, and second registered identification information; and
one or more processors configured to execute the instructions to:
collate first biological information of a user with the first registered biological information, the first biological information indicating a feature amount related to at least one of a fingerprint, an iris, a face, a voice, and a vein of the user;
allow an application to execute based on a collating result related to the first biological information;
acquire second biological information when the application executes, the second biological information being an external ear acoustic feature amount, by:
outputting a first signal to a device worn by the user, the first signal having a predetermined frequency;
receiving a second signal echoed in a part of body of the user; and
calculating the second biological information based on the second signal;
and perform a predetermined action of the application based on a status of the second biological information acquisition.

5. The personal authentication device according to claim 4, wherein the one or more processors further execute the instructions to:
terminate the application in response to failing to acquire the second biological information.

6. The personal authentication device according to claim 4, wherein the one or more processors further execute the instructions to:
collating the second biological information with the second registered biological information; and
identify an individual based on the collating result related to the first biological information and a collating result related to the second biological information.

7. A non-transitory computer readable recording medium storing a personal authentication program executable by a computer to perform:
collating first biological information of a user with first registered biological information, the first biological information indicating a feature amount related to at least one of a fingerprint, an iris, a face, a voice, and a vein of the user;
allowing an application to execute based on a collating result related to the first biological information;
acquiring second biological information when the application executes, the second biological information being an external ear acoustic feature amount, by:
outputting a first signal to a device worn by the user, the first signal having a predetermined frequency;
receiving a second signal echoed in a part of body of the user; and
calculating the second biological information based on the second signal; and
performing a predetermined action of the application based on a status of the second biological information acquisition.

8. The recording medium according to claim 7, wherein the personal authentication program is executable by the computer to further perform:
terminating the application in response to failing to acquire the second biological information.

9. The recording medium according to claim 7, wherein the personal authentication program is executable by the computer to further perform:
collating the second biological information with second registered biological information; and
identifying an individual based on the collating result related to the first biological information and a collating result related to the second biological information.

* * * * *